(12) United States Patent
Pierre et al.

(10) Patent No.: US 9,822,324 B2
(45) Date of Patent: Nov. 21, 2017

(54) AMINE ALKOXYLATE COMPOSITIONS AND THEIR USE AS LUBRICANT ADDITIVES

(71) Applicant: Dow Global Technologies LLC, Midland, MI (US)

(72) Inventors: Cynthia Pierre, Naperville, IL (US); Stephen W. King, League City, TX (US); Daniel A. Aguilar, Lake Jackson, TX (US); Brian A. Jazdzewski, Pearland, TX (US); John B. Cuthbert, Midland, MI (US); Paul R. Elowe, Midland, MI (US); Ashwin R. Bharadwaj, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 266 days.

(21) Appl. No.: 14/429,102

(22) PCT Filed: Oct. 15, 2013

(86) PCT No.: PCT/US2013/064902
§ 371 (c)(1),
(2) Date: Mar. 18, 2015

(87) PCT Pub. No.: WO2014/066088
PCT Pub. Date: May 1, 2014

(65) Prior Publication Data
US 2015/0232776 A1 Aug. 20, 2015

Related U.S. Application Data

(60) Provisional application No. 61/717,663, filed on Oct. 24, 2012.

(51) Int. Cl.
*C10M 133/40* (2006.01)
*C07D 241/02* (2006.01)
*C07D 295/13* (2006.01)

(52) U.S. Cl.
CPC ......... *C10M 133/40* (2013.01); *C07D 295/13* (2013.01)

(58) Field of Classification Search
CPC .................. C07D 241/08; C10M 2215/221
USPC .......................................... 508/255; 544/357
See application file for complete search history.

(56) References Cited

U.S. PATENT DOCUMENTS

2005/0172543 A1  8/2005  Muir
2008/0004362 A1  1/2008  Masuda et al.

FOREIGN PATENT DOCUMENTS

WO   2012040174   3/2012
WO   2013102053   7/2013

*Primary Examiner* — Vishal Vasisth
(74) *Attorney, Agent, or Firm* — Brooks, Cameron & Huebsch, PLLC

(57) ABSTRACT

Provided are compositions and their use as dispersant and/or detergent additives for lubricants. The compositions comprise an amine alkoxylate of the formula I: (I) wherein $R^1$-$R^7$, $R^{1'}$-$R^7$; x, x', A, A' and A" are as defined herein.

(I)

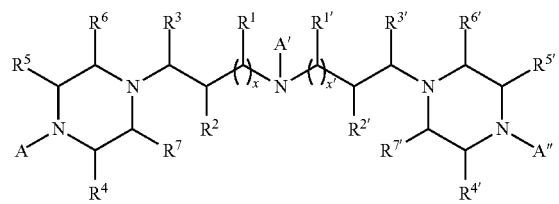

11 Claims, 4 Drawing Sheets

AMINE ALKOXYLATE COMPOSITIONS AND THEIR USE AS LUBRICANT ADDITIVES

This application is a 371 of PCT/US2013/064902, filed Oct. 15, 2013 which claims benefit of 61/717,663, filed Oct. 24, 2012.

FIELD

This invention relates generally to alkoxylate compositions and their use as dispersant and/or detergent additives for lubricants in fuel burning engines. More particularly, the invention relates to amine alkoxylate compositions for use in such applications.

BACKGROUND

Modern lubricants find use in a wide variety of applications. Lubricants can have various functions, including controlling friction between surfaces of moving parts, reducing wear of moving parts, reducing corrosion of surfaces of moving parts, particularly metal surfaces, damping mechanical shock in gears, and forming a seal on the walls of engine cylinders. A lubricant composition contains a base oil and typically one or more additives or modifiers that provide additional performance properties to the lubricant composition.

Soot or sludge formation is a widely encountered problem with many lubricants, particularly those that are used in fuel burning engines, such as automotive engines, marine engines, railroad engines, power plant diesels, and the like. Soot is formed from incomplete combustion in engine and exhaust systems. Soot particles can lead to an increase in the viscosity of the lubricant, deposition of contaminants onto metal surfaces, and soot induced wear. Thus, control of soot is an important performance attribute for lubricants used in fuel burning engines.

Soot control may generally be provided through inclusion of dispersants, detergents, or both in the lubricant. Dispersants suspend soot and similar contaminants in the bulk oil, thereby preventing an increase in engine oil (lubricant) viscosity. Detergents are primarily designed to neutralize combustion products; through neutralization of those species, detergents inhibit rust and corrosion and high temperature deposits.

Conventional dispersants and detergents are often lacking for a number of reasons, including the inability to provide the desired performance properties, processing problems, overall performance per cost, or the inability to optimize properties based on specific end-use performance characteristics. For example, viscometrics and low temperature properties are important variables in the final product and dispersants and detergents with broader flexibility offer processing advantages to the formulator. Additionally, many dispersants were developed for hydrocarbon based lubricants and show incompatibility with polyalkylene glycol base oils due to their low solubility in polyalkylene glycols.

The problem addressed by this invention is the provision of new compositions that are useful as dispersants and/or detergent additives for engine lubricants.

STATEMENT OF INVENTION

We have now found that amine alkoxylates as described herein impart various desirable properties to an engine lubricant, including one or more of improved soot suspension, increased basicity, greater processing flexibility, compatibility with other additives, and/or greater solubility in polyalkylene glycol base oils. Advantageously the amine alkoxylates of the invention are viable alternatives to existing materials for use as dispersants, detergents, or both in lubricant formulations. In particular, they may be used in applications for controlling soot build-up typically associated with engines for fossil or synthetic fuel burning and power generation.

In one aspect, therefore, there is provided a composition comprising an amine alkoxylate of formula I:

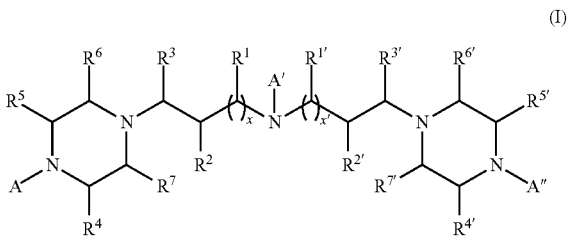

(I)

wherein $R^1$-$R^7$ and $R^{1'}$-$R^{7'}$ are independently hydrogen or hydrocarbyl groups; x and x' are independently 0 (a covalent bond) or an integer in the range of 1-10, and if x or x' is greater than 1, then $R^1$ and $R^{1'}$ are the same or different; and A, A' and A" are independently alkoxylate homopolymer or copolymer chains where the alkyl of the alkoxylate units is independently selected from $CH_2CH_2$, $CH_2CH(CH_3)$, $CH(CH_3)CH_2$, $CH_2CH(CH_2CH_3)$, or $CH(CH_2CH_3)CH_2$ groups. A, A' and A" can be hydroxyl terminated or hydroxyl terminated, but are typically hydroxyl terminated. The copolymer option for A, A' and A" can be selected from block copolymers and random copolymers.

Desirably, A, A' and/or A" are each independently of the form:

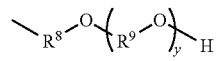

where y is independently selected for each of A, A' and A" from an integer ranging from 0 to 250; and $R^8$ and $R^9$ are independently selected for each of A, A' and A" from a group consisting of $CH_2CH_2$, $CH_2CH(CH_3)$, $CH(CH_3)CH_2$, $CH_2CH(CH_2CH_3)$, or $CH(CH_2CH_3)CH_2$, wherein if y is greater than 1, then each corresponding $R^9$ is the same or different and in the event they are different they may be in random or block configuration so as to form the following structure:

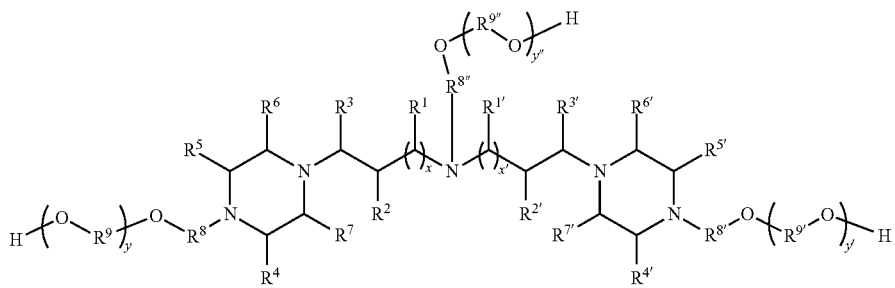

wherein $R^1$-$R^7$ and $R^{1'}$-$R^{7'}$ are independently hydrogen or hydrocarbyl groups; x and x' are independently 0 (a covalent bond) or an integer in the range of 1-10, and if x or x' is greater than 1, then $R^1$ and $R^{1'}$ are the same or different; y, y', or y" are independently an integer ranging from 0 to 250; and $R^8$, $R^{8'}$, $R^{8''}$, $R^9$, $R^{9'}$, and $R^{9''}$ when present are independently $CH_2CH_2$, $CH_2CH(CH_3)$, $CH(CH_3)CH_2$, $CH_2CH(CH_2CH_3)$, or $CH(CH_2CH_3)CH_2$, wherein if y, y', or y" is greater than 1, then each corresponding $R^9$, $R^{9'}$, or $R^{9''}$ is the same or different and in the event they are different they may be in random or block configuration.

In another aspect, there is provided a lubricant formulation comprising: a base oil; and a performance additive comprising an amine alkoxylate composition as described herein.

In a further aspect, there is provided a method for providing dispersancy, detergency, or both to a lubricant formulation for use in a fuel burning engine, the method comprising: including in the lubricant formulation an amine alkoxylate composition as described herein.

DETAILED DESCRIPTION

Figure 1:
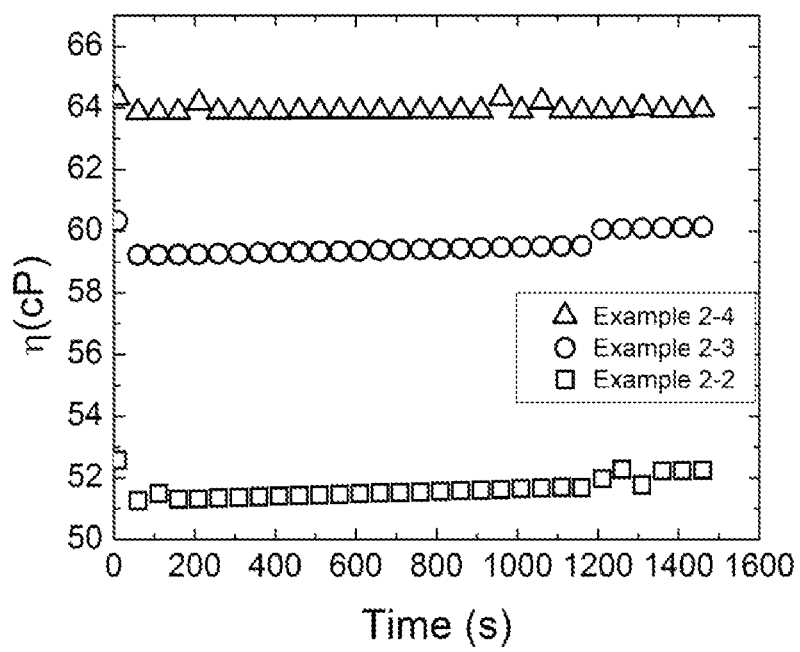
FIG. 1 is a plot showing viscosity as a function of time for constant shear stress of 2.65 Pa-s for exemplary lubricant formulations of the invention.

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

Ethyleneoxy or EO refers to —$CH_2$—$CH_2$—O—, propyleneoxy or PO refers to —$CH_2$—$CH(CH_3)$—O— or —$CH(CH_3)$—$CH_2$—O—, and butyleneoxy or BO refers to —$CH_2$—$CH(CH_2CH_3)$—O— or —$CH(CH_2CH_3)$—$CH_2$—O—.

"Hydrocarbyl" means substituted or unsubstituted, linear, branched, or cyclic aliphatic or aromatic hydrocarbyl such as alkyl, cycloalkyl, aryl, aralkyl, or the like; a monovalent moiety including one or more heteroatoms; polyether chains comprising one or more oxyalkylene repeating units such as —$R^M$O—, wherein $R^M$ is often alkylene of 2 to 5 carbon atoms; other oligomeric or polymer chains of at least 2 repeating units. Preferred hydrocarbyl groups include linear, branched, or cyclic hydrocarbyl such as alkyl of 1 to 10 carbon atoms, preferably 1 to 3 carbon atoms.

As noted above, the invention provides compositions that function as dispersant or detergent (or both) additives for lubricant formulations. The composition comprises an amine alkoxylate of formula I:

(I)

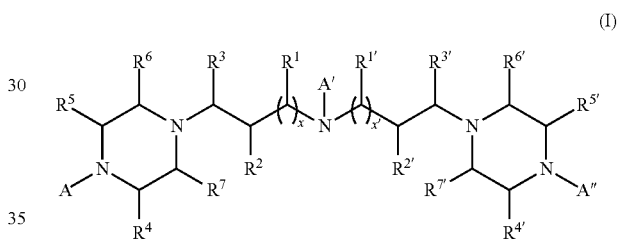

wherein $R^1$-$R^7$ and $R^{1'}$-$R^{7'}$ are independently hydrogen or hydrocarbyl groups; x and x' are independently 0 (a covalent bond) or an integer in the range of 1-10, and if x or x' is greater than 1, then $R^1$ and $R^{1'}$ are the same or different; and A, A' and A" are independently alkoxylate homopolymer or copolymer chains where the alkyl of the alkoxylate units is independently selected from $CH_2CH_2$, $CH_2CH(CH_3)$, $CH(CH_3)CH_2$, $CH_2CH(CH_2CH_3)$, or $CH(CH_2CH_3)CH_2$ groups. A, A' and A" can be hydroxyl terminated or hydroxyl terminated, but are typically hydroxyl terminated. The copolymer option for A, A' and A" can be selected from block copolymers and random copolymers.

Desirably, A, A' and/or A" are each independently of the form:

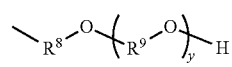

where y is independently selected for each of A, A' and A" from an integer ranging from 0 to 250; and $R^8$ and $R^9$ are independently selected for each of A, A' and A" from a group consisting of $CH_2CH_2$, $CH_2CH(CH_3)$, $CH(CH_3)CH_2$, $CH_2CH(CH_2CH_3)$, or $CH(CH_2CH_3)CH_2$, wherein if y is greater than 1, then each corresponding $R^9$ is the same or different and in the event they are different they may be in random or block configuration so as to form the following structure:

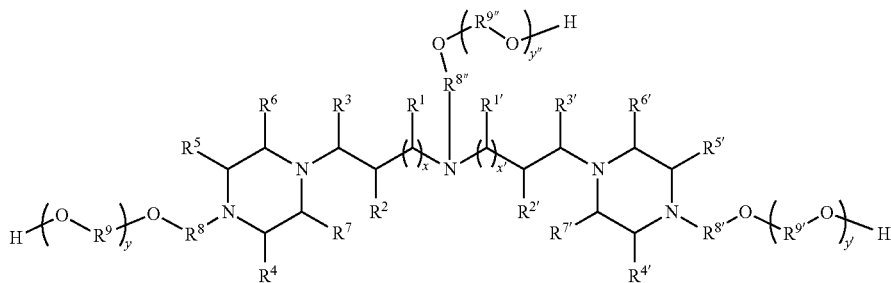

wherein $R^1$-$R^7$, $R^{1'}$-$R^{7'}$; x, x', $R^8$ $R^{8'}$, $R^{8''}$, $R^9$, $R^{9'}$, $R^{9''}$, y y', and y" are as defined above.

The A, A' and A" groups, including —O—$R^9$—, —O—$R^{9'}$—, and —O—$R^{9''}$— groups, in the amine alkoxylates of the invention are alkoxylate moieties that are derived from ethylene oxide, propylene oxide, and/or butylene oxide. It should be noted that when any of y y', or y" is greater than 1, then the corresponding moiety within the parentheses may contain the same or different alkoxylate groups. Moreover, the alkoxylate groups may be in block or random configuration. For instance, examples of suitable forms of A, A' and A" include, but are not limited to, H—$PO_6$—, H-EO-EO-PO-PO-EO-EO—, H-EO-PO-PO-EO-PO-EO—, H-PO-PO-EO-EO-BO-BO—, etc.

In some embodiments, the amine alkoxylates of formula I are of the formula I-1, which are amine alkoxylates of formula I wherein $R^1$-$R^7$ and $R^{1'}$-$R^{7'}$ are independently hydrogen or linear or branched $C_1$-$C_6$ alkyl. Preferably, $R^1$-$R^7$ and $R^{1'}$-$R^{7'}$ are each hydrogen.

In some embodiments, the amine alkoxylates of formulae I and I-1 are of the formula I-2, which are amine alkoxylates of formula I or I-1 wherein x and x' are independently 0 (a covalent bond) or an integer in the range of 1-5, alternatively an integer in the range of 1-4. In some embodiments, x and x' are both zero. In some embodiments, x and x' are independently 1, 2, 3, or 4.

In some embodiments, the amine alkoxylates of formulae I, I-1, and I-2 are of the formula I-3, which are amine alkoxylates of formula I, I-1, or I-2 wherein $R^8$, $R^{8'}$, and $R^{8''}$ are the same. In some embodiments, $R^8$, $R^{8'}$, and $R^{8''}$ are $CH_2CH(CH_3)$ or $CH(CH_3)CH_2$.

In some embodiments, the amine alkoxylates of formulae I, I-1, I-2, and I-3 are of the formula I-4, which are amine alkoxylates of formula I, I-1, I-2, or I-3 wherein y, y', and y" are independently an integer ranging from 1 to 250, alternatively 1 to 150, or alternatively 1 to 60. In some embodiments, y, y', and y" are each independently at least 10, alternatively they are independently at least 25, or alternatively they are independently at least 50.

In some embodiments, the amine alkoxylates of formulae I, I-1, I-2, I-3, and I-4 are of the formula I-5, which are amine alkoxylates of formula I, I-1, I-2, I-3, or I-4 wherein the sum of y, y', and y" is 225 or less, alternatively 200 or less, alternatively 175 or less, alternatively 150 or less, alternatively 125 or less, or alternatively 100 or less. In some embodiments, the sum of y, y', and y" is from 60 to 120.

In some embodiments, the amine alkoxylates of formulae I, I-1, I-2, I-3, I-4, and I-5 are of the formula I-6, which are amine alkoxylates of formula I, I-1, I-2, I-3, I-4, or I-5 wherein $R^9$, $R^{9'}$, and $R^{9''}$ are each $CH_2CH(CH_3)$ or $CH(CH_3)CH_2$ (when y, y', and y" are respectively 1 or greater).

In some embodiments, the amine alkoxylates of formulae I, I-1, I-2, I-3, I-4, I-5, and I-6 are of the formula I-7, which are amine alkoxylates of formula I, I-1, I-2, I-3, I-4, I-5, or I-6 having a number average molecular weight of at least 280 g/mol, alternatively at least 1000 g/mol, alternatively at least 3000 g/mol, alternatively at least 5000 g/mol, alternatively at least 8000 g/mol, or alternatively greater than 8000 g/mol.

In some embodiments, the amine alkoxylates of formulae I, I-1, I-2, I-3, I-4, I-5, I-6, and I-7 are of the formula I-8, which are amine alkoxylates of formula I, I-1, I-2, I-3, I-4, I-5, I-6, or I-7 having a number average molecular weight of 10,000 g/mol or less.

In some embodiments, the amine alkoxylates of formula I, I-1, I-2, I-3, I-4, I-5, I-6, I-7, or I-8 are of the formula II:

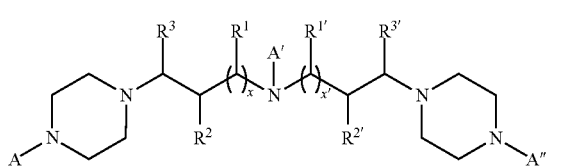

(II)

wherein $R^1$-$R^3$ and $R^{1'}$-$R^{3'}$ are independently hydrogen or linear or branched $C_1$-$C_6$ alkyl; x and x' are independently 0 (a covalent bond) or an integer in the range of 1-10 (preferably they are 0 or 1-4), and if x or x' is greater than 1, then $R^1$ and $R^{1'}$ are the same or different; and A, A' and A" are as defined for formula I.

Desirably, formula II take the form of formula II':

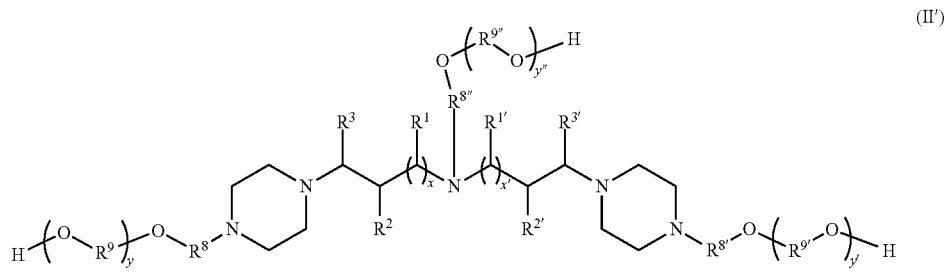

(II')

wherein $R^1$-$R^3$ and $R^{1'}$-$R^{3'}$ are independently hydrogen or linear or branched $C_1$-$C_6$ alkyl; x and x' are independently 0 (a covalent bond) or an integer in the range of 1-10 (preferably they are 0 or 1-4), and if x or x' is greater than 1, then $R^1$ and $R^{1'}$ are the same or different; y y', or y" are independently an integer ranging from 0 to 250 (preferably 1 to 250); and $R^8$ $R^{8'}$, $R^{8''}$, $R^9$, $R^{9'}$, and $R^{9''}$ when present are independently $CH_2CH_2$, $CH_2CH(CH_3)$, $CH(CH_3)CH_2$, $CH_2CH(CH_2CH_3)$, or $CH(CH_2CH_3)CH_2$, wherein if y y', or y" is greater than 1, then each corresponding $R^9$, $R^{9'}$, or $R^{9''}$ is the same or different and in the event they are different they may be in random or block configuration.

In some embodiments, the amine alkoxylates of formula I, I-1, I-2, I-3, I-3, I-4, I-5, I-6, I-7, I-8, or II are of the formula II-1:

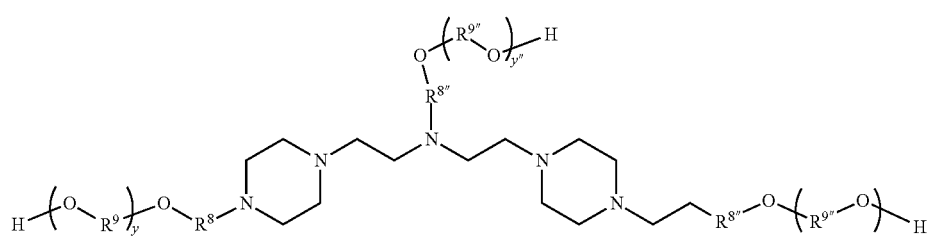

(II-1)

wherein y y', or y" are independently an integer ranging from 0 to 250, preferably 1 to 250; and $R^8$ $R^{8'}$, $R^{8''}$, $R^9$, $R^{9'}$, and $R^{9''}$ are independently $CH_2CH_2$, $CH_2CH(CH_3)$, $CH(CH_3)CH_2$, $CH_2CH(CH_2CH_3)$, or $CH(CH_2CH_3)CH_2$, wherein if y y', or y" is greater than 1, then each corresponding $R^9$, $R^{9'}$, or $R^{9''}$ is the same or different and in the event they are different they may be in random or block configuration.

In some embodiments of the invention, the composition (including any of the embodiments described above) further comprises an amine alkoxylate of the formula III:

wherein $R^1$-$R^7$ and $R^{1'}$-$R^{7'}$ are independently hydrogen or hydrocarbyl groups;

x and x' are independently 0 (a covalent bond) or an integer in the range of 1-10, and if x or x' is greater than 1, then $R^1$ and $R^{1'}$ are the same or different;

y y', or y" are independently an integer ranging from 0 to 250; and $R^8$ $R^{8'}$, $R^{8''}$, $R^9$, $R^{9'}$, and $R^{9''}$ are independently $CH_2CH_2$, $CH_2CH(CH_3)$, $CH(CH_3)CH_2$, $CH_2CH(CH_2CH_3)$, or $CH(CH_2CH_3)CH_2$, wherein if y y', or y" is greater than 1, then each corresponding $R^9$, $R^{9'}$, or $R^{9''}$ is the same or different and in the event they are different they may be in random or block configuration.

In some embodiments, when the amine alkoxylate of formula III is present in the composition, the amount of the formula III amine alkoxylate may be from 2 to 5 weight percent, based on the total weight of the formula I and formula III alkoxylates.

In some embodiments, the amine alkoxylates of formula III are of the formula III-1, which are amine alkoxylates of formula III wherein $R^1$-$R^7$ and $R^{1'}$-$R^{7'}$ are independently hydrogen or linear or branched $C_1$-$C_6$ alkyl. Preferably, $R^1$-$R^7$ and $R^{1'}$-$R^{7'}$ are each hydrogen.

In some embodiments, the amine alkoxylates of formulae III and III-1 are of the formula III-2, which are amine

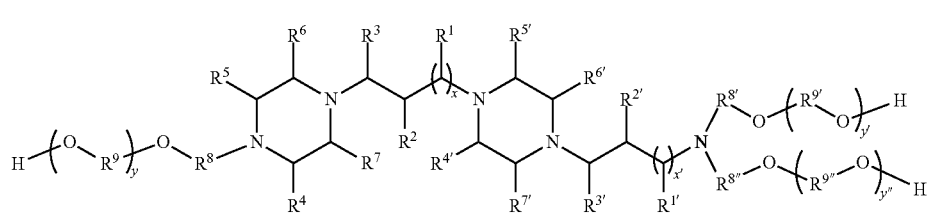

(III)

alkoxylates of formula III or III-1 wherein x and x' are independently 0 (a covalent bond) or an integer in the range of 1-5, alternatively an integer in the range of 1-4. In some embodiments, x and x' are both zero. In some embodiments, x and x' are independently 1, 2, 3, or 4.

In some embodiments, the amine alkoxylates of formulae III, III-1, and III-2 are of the formula III-3, which are amine alkoxylates of formula III, III-1, or III-2 wherein $R^8$, $R^{8'}$, and $R^{8''}$ are the same. In some embodiments, $R^8$, $R^{8'}$, and $R^{8''}$ are $CH_2CH(CH_3)$ or $CH(CH_3)CH_2$.

In some embodiments, the amine alkoxylates of formulae III, III-1, III-2, III-3 are of the formula III-4, which are amine alkoxylates of formula III, III-1, III-2, or III-3 wherein y, y', and y'' are independently an integer ranging from 1 to 250, alternatively 1 to 150, or alternatively 1 to 60. In some embodiments, y, y', and y'' are each independently at least 10, alternatively they are independently at least 25, alternatively they are independently at least 50, alternatively they are independently at least 75, or alternatively they are independently at least 100.

In some embodiments, the amine alkoxylates of formulae III, III-1, III-2, III-3, and III-4 are of the formula III-5, which are amine alkoxylates of formula III, III-1, III-2, III-3, or III-4 wherein the sum of y, y', and y'' is 225 or less, alternatively 200 or less, alternatively 175 or less, alternatively 150 or less, alternatively 125 or less, or alternatively 100 or less. In some embodiments, the sum of y, y', and y'' is from 60 to 120.

In some embodiments, the amine alkoxylates of formulae III, III-1, III-2, III-3, III-4, and III-5 are of the formula III-6, which are amine alkoxylates of formula III, III-1, III-2, 111-3, III-4, or III-5 wherein $R^9$, $R^{9'}$, and $R^{9''}$ are each $CH_2CH(CH_3)$ or $CH(CH_3)CH_2$ (when y, y', and y'' are respectively 1 or greater).

In some embodiments, the amine alkoxylates of formulae III, III-1, III-2, III-3, III-4, III-5, and III-6 are of the formula III-7, which are amine alkoxylates of formula III, III-1, III-2, III-3, III-4, 111-5, or III-6 having a number average molecular weight of at least 280 g/mol, alternatively at least 1000 g/mol, alternatively at least 3000 g/mol, alternatively at least 5000 g/mol, alternatively at least 8000 g/mol, or alternatively greater than 8000 g/mol.

In some embodiments, the amine alkoxylates of formulae III, III-1, III-2, III-3, III-4, III-5, III-6, and III-7 are of the formula III-8, which are amine alkoxylates of formula III, III-1, III-2, III-3, III-4, 111-5, III-6, or III-7 having a number average molecular weight of 10,000 g/mol or less.

The amine alkoxylates of the invention are prepared by first synthesizing the underlying cyclic polyamine compound and then alkoxylating the cyclic polyamine compound in the presence of ethylene oxide, propylene oxide, and/or butylene oxide. The cyclic polyamine is typically of the following formula A or B:

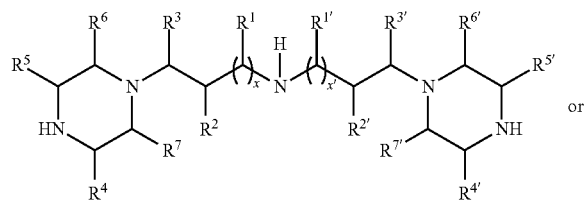
(A)

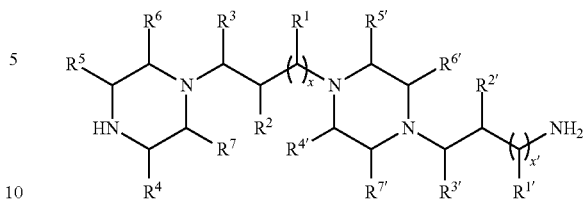
(B)

wherein $R^1$-$R^7$, $R^{1'}$-$R^{7'}$; x, and x' are as defined above.

Cyclic polyamines of the formulae A and B may be made according to processes described in commonly assigned U.S. Provisional Patent Application Ser. No. 61/581,323 entitled Formation of Higher Molecular Weight Cyclic Polyamine Compounds From Cyclic Polyamine Compounds, filed Dec. 29, 2011 (King), which application is incorporated herein by reference. U.S. 61/581,323 describes processes of transaminating a first cyclic polyamine compound of the formula:

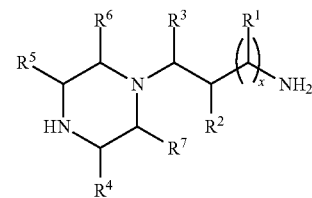

in the presence of a catalyst under conditions effective to cause the formation of the cyclic polyamines of formula A and B. Suitable catalysts for the transamination may include, for instance, nickel (Ni), copper (Cu), cobalt (Co), ruthenium (Ru), rhenium (Re), rhodium (Rh), platinum (Pt), palladium (Pd), iridium, or combinations thereof. A preferred catalyst may comprise Ni and Re in a ratio in the range of 3:1 to 14:1 on an alumina-silica support. The process may be carried out, for example, at elevated pressure, e.g., 300-1000 psi, and at elevated temperature, e.g., 100-220° C. in the presence of hydrogen at a level of, for example, from 0.1 to 100 mole percent of the reaction mixture.

The cyclic polyamines contained in the reaction product mixture may be separated (refined) by any method known in the art, for example, using conventional distillation technology, including dividing wall columns. Other separation techniques such as membrane separation, melt crystallization, and reactive distillation may also be employed.

Examples of first cyclic polyamines useful in the above process include 2-(piperazin-1-yl)ethanamine (AEP), 3-(piperazin-1-yl)propan-1-amine, 4-(piperazin-1-yl)butan-1-amine, 5-(piperazin-1-yl)pentan-1-amine, 6-(piperazin-1-yl)hexan-1-amine, 1-(piperazin-1-yl)propan-2-amine and 2-(piperazin-1-yl)propan-1-amine.

Examples of cyclic polyamines of formula A include bis(2-(piperazin-1-yl)ethyl)amine (BPEA), (3-(piperazin-1-yl)propyl)amine, bis(4-(piperazin-1-yl)butyl)amine, bis(5-(piperazin-1-yl)pentyl)amine, bis(6-(piperazin-1-yl)hexyl) amine, bis(1-(piperazin-1-yl)propan-2-yl)amine, and bis(2-(piperazin-1-yl)propyl)amine.

Examples of cyclic polyamines of Formula B include 2-(4-(2-(piperazin-1-yl)ethyl)piperazin-1-yl)ethanamine, 3-(4-(3-(piperazin-1-yl)propyl)piperazin-1-yl)propan-1- amine, 4-(4-(4-(piperazin-1-yl)butyl)piperazin-1-yl)butan-1-amine, 5-(4-(5-(piperazin-1-yl)pentyl)piperazin-1-yl)pentan-1-amine, 6-(4-(6-(piperazin-1-yl)hexyl)piperazin-1-yl)hexan-1-amine, 1-(4-(1-(piperazin-1-yl)propan-2-yl)piperazin-1-yl)propan-2-amine, and 2-(4-(2-(piperazin-1-yl)propyl)piperazin-1-yl)propan-1-amine.

Amine alkoxylates as described above may be prepared by the alkoxylation of the underlying cyclic polyamines of formula A or B. In a typical procedure, the cyclic polyamine is alkoxylated with alkylene oxide compounds (ethylene oxide, propylene oxide, and/or butylene oxide). Alkoxylation processes may, for instance, be carried out in the presence of acidic or alkaline catalysts or, in the case of direct amine alkoxylation, the reaction may auto-catalyze (and therefore no additional catalyst is needed). Alkaline catalysts may include, for instance, hydroxides or alcoholates of sodium or potassium, including NaOH, KOH, sodium methoxide, potassium methoxide, sodium ethoxide and potassium ethoxide. Base catalysts are normally used in a concentration of from 0.05 percent to about 5 percent by weight, preferably about 0.1 percent to about 1 percent by weight based on starting material.

The addition of alkylene oxides may, for instance, be carried out in an autoclave under pressures from about 10 psig to about 200 psig, preferably from about 60 to about 100 psig. The temperature of alkoxylation may range from about 30° C. to about 200° C., preferably from about 100° C. to about 160° C. After completion of oxide feeds, the product is typically allowed to react until the residual oxide is less than about 10 ppm. After cooling the reactor to an appropriate temperature ranging from about 20° C. to 130° C., the residual catalyst may be left unneutralized, or neutralized with organic acids, such as acetic, propionic, or citric acid. Alternatively, the product may be neutralized with inorganic acids, such as phosphoric acid or carbon dioxide. Residual catalyst may also be removed using ion exchange or an adsorption media, such as diatomaceous earth.

Compositions of the invention are useful as performance additives for lubricant formulations (also referred to herein as engine oils). More specifically, the compositions function as dispersants and/or detergents in lubricant formulations for fuel burning engines (particularly in components of an engine where soot accumulation may occur). Thus, a lubricant formulation according to the invention comprises an amine alkoxylate as described above together with a base oil (lubricating oil).

Base oils useful in the lubricant formulations may be derived from synthetic or natural sources and include, without limitation, mineral oil or synthetic oils. Mineral oil includes paraffinic, naphthenic and other oils that are ordinarily used in lubricating oil compositions. Useful synthetic oils include, without limitation, synthetic esters, polyalphaolefins (PAO) and polyalkylene glycols (PAG). Synthetic esters may include the esters of monocarboxylic acids and polycarboxylic acids, as well as monohydroxy alkanols and polyols. Blends of oils, such as blends of mineral oils with synthetic oils are also useful. Preferably, the base oil contains a polyalkylene glycol.

The lubricant formulations of the invention are suitable for use in fuel burning engines (e.g., diesel or gasoline), such as automotive engines, marine engines, railroad engines, power plant diesels, and the like, and particularly in components of such engines where soot generation may occur. Preferably, the lubricant formulations are for use in diesel engines. Typically, the lubricant resides (at rest) in the crankcase of an engine.

The base oil selected for the formulation should be of viscosity suitable for use in the particular application. A person of ordinary skill in the art can readily determine the appropriate viscosity. For instance, base oils for use in the crankcase of internal combustion engines, such as gasoline engines and diesel engines, including marine engines, may typically have a kinematic viscosity of about 4 cSt to 32 cSt, preferably about 7 cSt to 11 cSt, at 100° C.

The lubricant formulation may include further additives conventionally used in lubricating oil formulations, such as detergents, foam inhibitors, extreme pressure and antiwear agents, rust inhibitors, antioxidants, and similar materials.

A person of ordinary skill in the art can readily determine the effective amount of the amine alkoxylate composition of the invention that should be used in a particular lubricant formulation, via a combination of general knowledge of the applicable field as well as routine experimentation where needed. By way of non-limiting example, suitable amounts may include from 0.5 to 15 percent by weight based on the total weight of the lubricant formulation. By way of further example, if the primary function of the amine alkoxylate is as a dispersant, a suitable amount may include from 2 to 10 weight percent based on the total weight of the lubricant formulation. By way of still further example, if the primary function of the amine alkoxylate is as a detergent, a suitable amount may include from 0.5 to 7 weight percent, alternatively 0.75 to 4 weight percent, based on the total weight of the lubricant formulation.

Some embodiments of the invention will now be described in detail in the following Examples.

EXAMPLES

Example 1: Synthesis of bis(2-(piperazin-1-yl)ethyl)amine (BPEA)

A fixed bed plug flow reactor is packed with a Ni (6.8 wt. percent)/Re (1.8 wt. percent) loaded alumina (80 wt. percent)-silica (20 wt. percent) catalyst. 2-(Piperazin-1-yl)ethanamine (AEP) and hydrogen (1.0-1.5 mole percent based on AEP feed) are fed to the reactor at 800 psig and temperatures of 140-165° C. The crude reaction mixture is distilled to give ≥95 percent (area percent by gas chromatography) bis(2-(piperazin-1-yl)ethyl)amine (BPEA). The material is also analyzed by electrospray ionization liquid chromatography mass spectrometry (ESI-LC-MS). The positive ion mass spectrum shows a peak at 242.2.

Example 2: Propoxylation of BPEA

Alkoxylation reactions are performed in a jacketed, baffled 9 L stainless steel (SS) autoclave reactor equipped with magnetically driven impeller, pressure transducer, jacket return line thermocouple and redundant reactor thermocouples. Temperature control is achieved with a mixture of steam and cooling water to the reactor jacket introduced via control valves operated by a MOD-V digital control system. Oxide addition is effected by charging propylene oxide into a designated feed tank situated on a scale. Oxide is metered from the feed tank bottom outlet to the reactor through an automated flow control valve within the operating temperature (±5° C. of set point) and pressure (16-85 psia) constraints.

The following runs target the propoxylation of bis-N (piperazinylethyl)amine (BPEA) with 3 propylene oxide (PO), 75 PO, 100 PO, and 150 PO. The initial BPEA+3 PO feed is conducted without added catalyst (amine autocatalytic), then the BPEA tripropoxylate is catalyzed with KOH and dehydrated prior to adding additional PO in a stepwise alkoxylation. The preparation described below is representative for all of the examples generated. The samples are characterized using hydroxyl content and water levels. Hydroxyl content is measured by derivatization of the polyglycol with an excess of phthalic anhydride reagent with imidazole catalyst in pyridine solvent at 100° C. for 30 minutes using a procedure based on ASTM D 4274. After formation of the phthalate half ester, the unreacted phthalic anhydride is hydrolyzed and titrated with 1N sodium hydroxide reagent using a Mettler DL-55 titrator. The half ester is quantified by the difference between the sample titration and a blank titration of the same amount of phthalic anhydride reagent completely hydrolyzed with water. The difference is expressed as hydroxyl number (mg KOH/g sample) or may be reported as % OH, which is (hydroxyl number)/33. For the BPEA propoxylates analyzed in this study, the molecular weight is calculated by the following formula: (3×1700)/% OH. Water levels are measured by volumetric Karl Fischer analysis using a Brinkmann 701 KF Titrino water titrator with Hydranal® Composite 5 reagent.

Preparation of Example 2-1

This run targeted the initial propoxylation (3 PO) of BPEA without added catalyst (amine autocatalytic) using a 115° C. feed temperature and a 120° C. digest temperature. Although not required to prepare the three mole propoxylate, a stepwise propoxylation using 0.75 equivalent PO increments was employed to obtain samples for NMR spectroscopic analysis in order to determine differences in reactivity between the ring and chain nitrogens.

Preparation of Example 2-2

BPEA tripropoxylate (Example 2-1, 330.00 g) and 45% potassium hydroxide (20.85 g) are charged to a 1 L pear shaped flask and dehydrated at 115° C. with vacuum for 6 hours on a laboratory rotary evaporator. The water content measured by Karl Fisher titration is 1394 ppm. The catalyzed dehydrated BPEA tripropoxylate (282.4 g) is charged into a previously nitrogen purged 9 L reactor. The reactor is pressurized then vented seven times to remove atmospheric oxygen, then pressurized with nitrogen to 16-20 psia at ambient temperature. The reactor contents are heated with agitation at 110° C., then propylene oxide (2850 g total) is metered into the reactor over approximately 10 hr at 110° C. resulting in an operating pressure of 80 psia. After the PO feed is complete, the reactor contents are agitated at 115° C. overnight (11.5 hr) to consume unreacted oxide (digest), then sampled. A portion of the reactor contents (630.8 g designated as Example 2-2) is neutralized with magnesium silicate, filtered, and measured for hydroxyl content (1.250% OH corresponding to 4080 MW or BPEA+66 PO).

Preparation of Example 2-3

The remaining 2501.6 g of reactor contents are heated with agitation to 110° C., then propylene oxide (896 g total) is metered into the reactor over approximately 4 hr resulting in an operating pressure of 75-80 psia. After the PO feed is complete, the reactor contents are agitated at 115° C. overnight (16 hr) to consume unreacted oxide, then cooled to 60° C. A portion of the reactor contents (617.5 g designated Example 2-3) is neutralized with magnesium silicate, filtered, and analyzed for hydroxyl content (0.984% OH corresponding to 5183 MW or BPEA+85 PO).

Preparation of Example 2-4

The remaining 2780.1 g of reactor contents are heated with agitation to 110° C., then propylene oxide (1205 g total) is metered into the reactor over 5.5 hr resulting in an operating pressure of approximately 80 psia. After the PO feed is complete, the reactor contents are agitated at 115° C. overnight (12 hr) to consume unreacted oxide, then cooled to 60° C. The reactor contents are drained (3967.3 g). A portion of the reactor contents designated as Example 2-4 is neutralized with magnesium silicate, filtered, and analyzed for hydroxyl content (0.829% OH corresponding to 6152 MW or BPEA+102 PO).

Example 3: Dispersant in Engine Oil

Carbon black is used as a substitute for diesel engine soot. To characterize the performance of a dispersant, 5 wt % of carbon black is added to the full engine oil formulation. A dispersant's efficacy can be gauged by measuring the viscosity of the dispersant in an engine oil formulation in the presence of carbon black. The ability of the dispersant to prevent viscosity increases or decreases indicates that the dispersant is able to stabilize the viscosity of the engine oil during operation.

Testing is carried out as follows (see Yamaguchi, E. "Voluminosities of EGR engine soot and carbon black: A bench test for fresh engine oils," Tribology and Lubrication Technology, 2008, pp 50-55.). An engine oil formulation (19 mL) is placed in a jacketed graduated cylinder and 1 gm (5 wt %) of Columbian Carbon Black Raven 1040 Powder is added to the formulation. The jacked cylinder is placed on a high shear mixer and cooled using water. The mixer is ramped manually from 0-17,500 rpm over 5 minutes. Once the mixer is at 17,500 rpm, the fluid is allowed to mix for 10 minutes. At the end of 10 minutes the mixer is turned off and the formulation-carbon black mixture transferred to a sample bottle.

The viscosity of the formulation-carbon black mixture is measured on Reologica Viscoanalyser controlled stress rheometer using a 4° cone and plate. All measurements are conducted at 40° C. In the first measurement, the sample is subjected to a continuous 2.65 Pa shear stress after 600 s equilibration time with nopre-shear. 30 viscosity readings are taken at 50 second intervals. The second measurement is conducted on the same sample, immediately after the completion of the first measurement. The sample is allowed to equilibrate for 300 seconds with no pre-shear. After equilibration a shear sweep from 0.1 to 50.87 Pa is done in 20 logarithmic increments. The goal of both experiments is to evaluate the efficacy of the dispersant on reducing or eliminating viscosity increases in the fluid.

Figure 2:
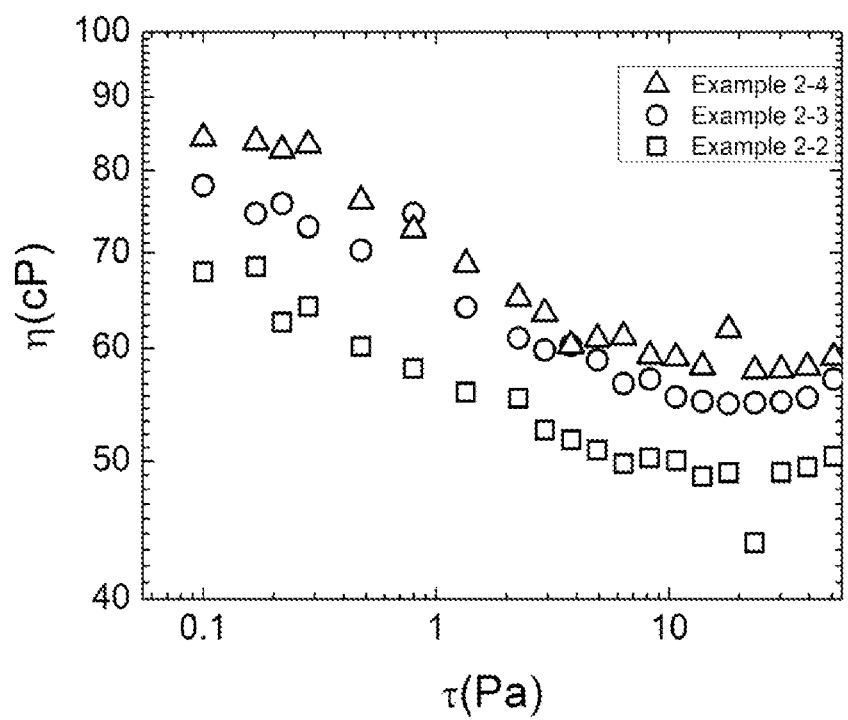
FIG. 2 is a plot showing viscosity as a function of shear stress for exemplary lubricant formulations of the invention.

The lubricant formulation of Table 1 is tested and the results are shown in FIGS. 1-4. FIG. 1 depicts the viscosity profile of the Examples 2-2, 2-3, and 2-4 in an engine oil formulation under constant shear stress; the viscosity of each example is constant over time, thereby, exhibiting viscosity independent of time at a constant shear stress. Moreover, the viscosity is nearly constant across all shear stresses of interest as shown in FIG. 2, suggesting that these examples exhibit Newtonian behavior. This result suggests that the carbon black particles were adequately dispersed throughout the formulation and consequently, agglomerates were not formed. These results demonstrate the potential of these invention examples as dispersants.

Figure 3:
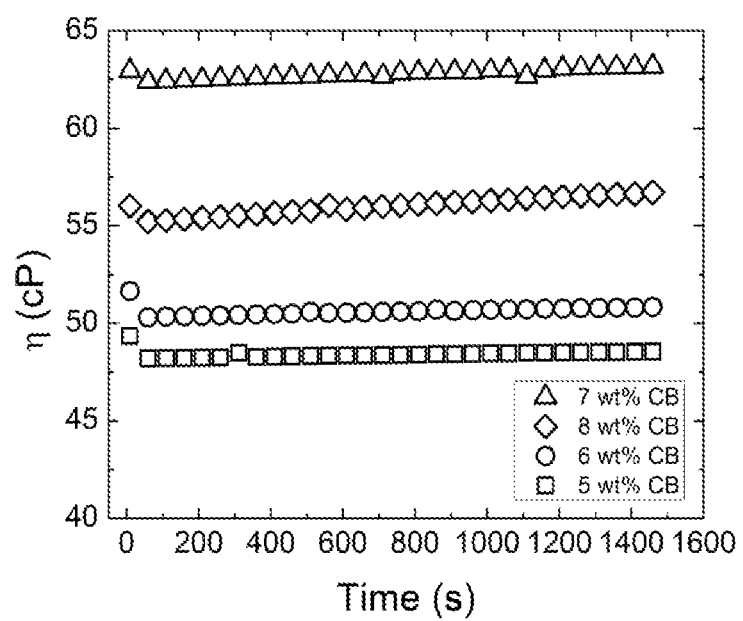
FIG. 3 is a plot showing viscosity as a function of time under a constant shear stress of 2.65 Pa-s for an exemplary lubricant formulation of the invention containing 5, 6, 7, and 8 wt % carbon black.
Figure 4:
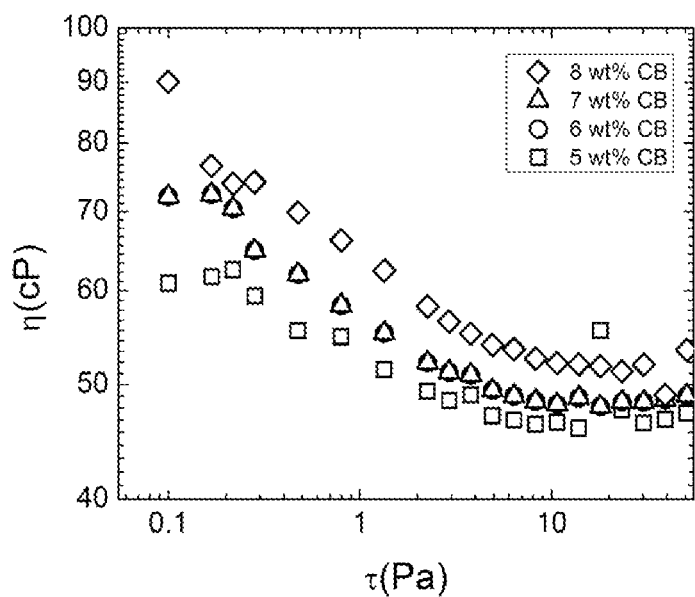
FIG. 4 is a plot showing effect of carbon black concentration on viscosity as a function of shear stress for an exemplary lubricant formulation of the invention containing 5, 6, 7, and 8 wt % carbon black.

FIGS. 3 and 4 show that Example 2-2 at 3 weight percent provides excellent soot dispersions at various soot concentrations, including the high concentration of 8 weight percent. The ability to disperse such high concentrations of soot in a lubricant at such low dispersant concentration is believed to be unique.

TABLE 1

Composition for Engine Oil Formulation Used for Rheology Testing

| Ingredient | Supplier | Function | Concentration (wt %) |
|---|---|---|---|
| UCON ™ LB-165\UCON ™ LB-285* | Dow | Base Fluid | Balance |
| N-phenyl-1-naphthylamine (PANA) | Aventis | Antioxidant | 0.60 |
| Irganox 5057 | Ciba SC | Antioxidant | 0.50 |
| Additin RC 7115 | RheinChemie | Antioxidant | 0.95 |
| Phenothiazine | CYTEC | Antioxidant | 0.20 |
| Tolyltriazole | BASF | Copper/Lead Inhibitor | 0.15 |
| Desmophen NH 1420 | Bayer MaterialScience | Acid Scavenger | 0.80 |
| Irgalube TPPT | Ciba SC | Extreme Pressure/Anti-Wear | 1.00 |
| Dibenzyl Disulfide | TCI America | Extreme Pressure | 0.30 |
| Dispersant | Various | Deposit Control | 5.00 |

*These are polyalkylene glycol (PAG) base oils. Ratio of UCON LB-165 to UCON LB-285 66.90 to 25.27.

Example 4: Functionality as Detergent for Deposit Control in an Engine Oil

The amine alkoxylate of Example 2-2 is formulated into a PAG engine oil shown in Table 2. The formulation is evaluated for deposit formation using a Panel Coker. The Panel Coker measures the tendency of engine oils to form coke when in contact with metal surfaces at high temperatures. Aluminum test panels are weighed and then heated to 600° F. During the test the engine oil is splashed on the aluminum surface for 8 hours at an agitation of 1000 rpm. After testing the test panel is dried and the weight is recorded. Lower mass is desired as that indicates fewer deposits formed.

TABLE 2

Composition for Engine Oil Formulation Used for Panel Coker Measurement

| Ingredient | Concentration (wt %) | Function |
|---|---|---|
| UCON LB-165\UCON LB285* | Balance | Base oil |
| N-phenyl-1-naphthylamine (PANA) | 0.61 | Antioxidant |
| Irganox 5057 | 0.51 | Antioxidant |
| Additin RC 7115 | 0.97 | Antioxidant |
| Phenothiazine | 0.20 | Antioxidant |
| Tolyltriazole | 0.15 | Copper/Lead Inhibitor |
| Desmophen NH-1420 | 0.81 | Acid Scavenger |
| Irgalube TPPT | 1.02 | Extreme Pressure/Anti-Wear |
| Dibenzyl Disulfide | 0.31 | Extreme Pressure |
| Example 2-2 | 3.25 | Dispersant |

*Ratio of UCON LB-165 to UCON LB-285 66.90 to 25.27.

Table 3 provides the deposit mass for a PAG engine oil without a dispersant, compared to engine oil containing the inventive Example 2-2 BPEA propoxylate and the a comparative material Valvoline Premium Blue (a commercially available mineral oil based lubricant containing a dispersant). The inventive material reduced the deposits to similar and slightly better than the competitive benchmark.

TABLE 3

Deposit Formation via Panel Coker

| Sample | Deposit (mg) |
|---|---|
| Engine oil (comparative) | 222.1 |
| Valvoline Premium Blue (comparative) | 120.8 |
| Engine oil + Example 2-2 (inventive) | 111.1 |

Example 5: Function as Detergent

Thermal and oxidative degradation of an engine oil leads to the formation of organic acids. Additives that increase the basicity of the engine oil are included to help neutralize these acidic degradation products, which are the precursors to varnish and deposits. If these acidic byproducts are not neutralized, increased corrosion and rust are likely occurrences due to their propensity to attack metal surfaces and form varnish and deposits. The total base number (TBN) is used to assess the ability of an additive to increase basicity. The test is conducted by dissolving the sample in an anhydrous mixture of chlorobenzene and glacial acetic acid and titrating the mixture with a solution of perchloric acid in glacial acetic acid using potentiometric titrimeter. A glass indicating electrode and a reference electrode, connected to the sample solution via a salt bridge, are used to record volumes of the titrating solution. The end point is taken at the inflection in the resulting curve.

Table 4 shows that Example 2-2 BPEA Propoxylate positively impacts total base number of the formulation.

TABLE 4

TBN of Various PAG Formulations with Different Additives

| Sample Composition | ASTM D2896 (mg KOH/g) |
|---|---|
| Control | 2.36 |
| Engine oil + 5 wt % BPEA Propoxylate (Example 2-2) | 3.85 |

The invention claimed is:

1. A composition comprising an amine alkoxylate of formula I:

(I)

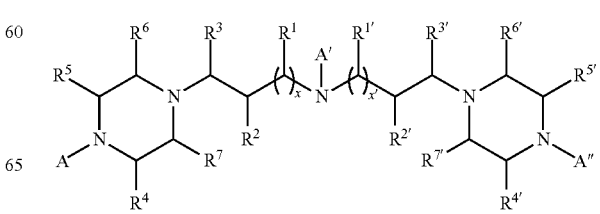

wherein $R^1$-$R^7$ and $R^{1'}$-$R^{7'}$ are independently hydrogen or hydrocarbyl groups; x and x' are independently 0 (a covalent bond) or an integer in the range of 1-10, and if x or x' is greater than 1, then $R^1$ and $R^{1'}$ are the same or different; and A, A' and A" are independently alkoxylate homopolymer or copolymer chains where the alkyl of the alkoxylate units is independently selected from $CH_2CH_2$, $CH_2CH(CH_3)$, $CH(CH_3)CH_2$, $CH_2CH(CH_2CH_3)$, or $CH(CH_2CH_3)CH_2$ groups.

2. The composition of claim 1, comprising an amine alkoxylate having the following structure:

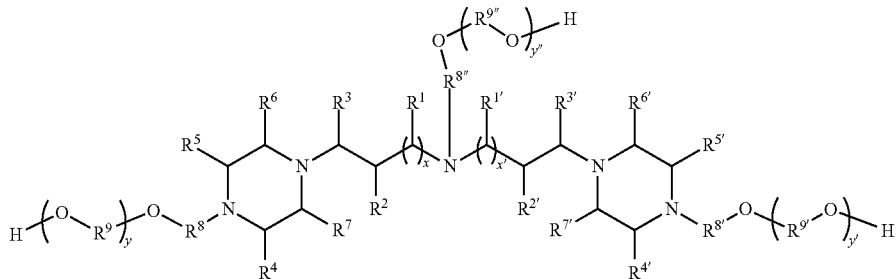

wherein $R^1$-$R^7$ and $R^{1'}$-$R^{7'}$ are independently hydrogen or hydrocarbyl groups;

x and x' are independently 0 (a covalent bond) or an integer in the range of 1-10, and if x or x' is greater than 1, then $R^1$ and $R^{1'}$ are the same or different;

y y', or y" are independently an integer ranging from 0 to 250; and $R^8$ $R^{8'}$, $R^{8''}$, $R^9$, $R^{9'}$, and $R^{9''}$ are independently $CH_2CH_2$, $CH_2CH(CH_3)$, $CH(CH_3)CH_2$, $CH_2CH(CH_2CH_3)$, or $CH(CH_2CH_3)CH_2$, wherein if y y', or y" is greater than 1, then each corresponding $R^9$, $R^{9'}$, or $R^{9''}$ is the same or different and in the event they are different they may be in random or block configuration.

3. The composition of claim 1 wherein $R^1$-$R^7$ and $R^{1'}$-$R^{7'}$ are independently hydrogen or linear or branched $C_1$-$C_6$ alkyl.

4. The composition of claim 1 wherein $R^1$-$R^7$ and $R^{1'}$-$R^{7'}$ are each hydrogen.

5. The composition of claim 1 wherein the amine alkoxylate is of the formula II:

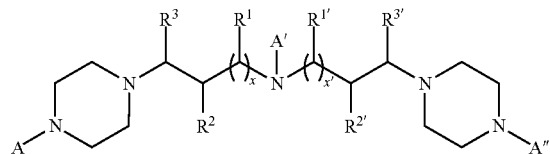

wherein $R^1$-$R^3$ and $R^{1'}$-$R^{3'}$ are independently hydrogen or linear or branched $C_1$-$C_6$ alkyl; x and x' are independently 0 (a covalent bond) or an integer in the range of 1-10 (preferably they are 0 or 1-4), and if x or x' is greater than 1, then $R^1$ and $R^{1'}$ are the same or different; and A, A' and A" are as defined for formula I.

6. The composition of claim 5 wherein the amine alkoxylate is of the formula II':

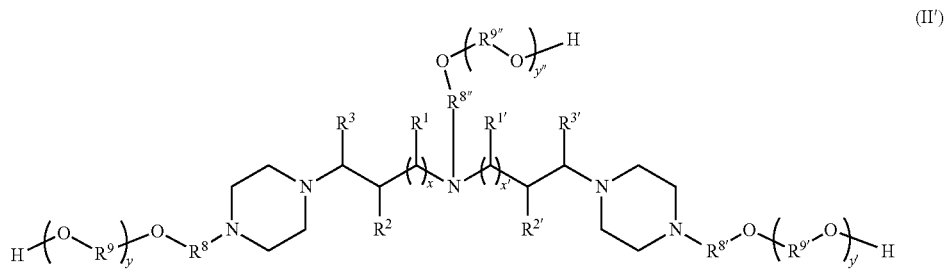

wherein $R^1$-$R^3$ and $R^{1'}$-$R^{3'}$ are independently hydrogen or linear or branched $C_1$-$C_6$ alkyl; x and x' are independently 0 (a covalent bond) or an integer in the range of 1-10, and if x or x' is greater than 1, then $R^1$ and $R^{1'}$ are the same or different; y y', or y" are independently an integer ranging from 0 to 250; and $R^8$ $R^{8'}$, $R^{8''}$, $R^9$, $R^{9'}$, and $R^{9''}$ are independently $CH_2CH_2$, $CH_2CH(CH_3)$, $CH(CH_3)CH_2$, $CH_2CH(CH_2CH_3)$, or $CH(CH_2CH_3)CH_2$, wherein if y y', or y" is greater than 1, then each corresponding $R^9$, $R^{9'}$, or $R^{9''}$ is the same or different and in the event they are different they may be in random or block configuration.

7. The composition of claim 2 wherein $R^8$, $R^{8'}$, $R^{8''}$, $R^9$, $R^{9'}$, and $R^{9''}$ are independently $CH_2CH(CH_3)$ or $CH(CH_3)CH_2$.

8. The composition of claim 1 wherein the amine alkoxylate has a number average molecular weight ranging from 280 to 10,000 g/mol.

9. The composition of claim 1 further comprising an amine alkoxylate of formula III:

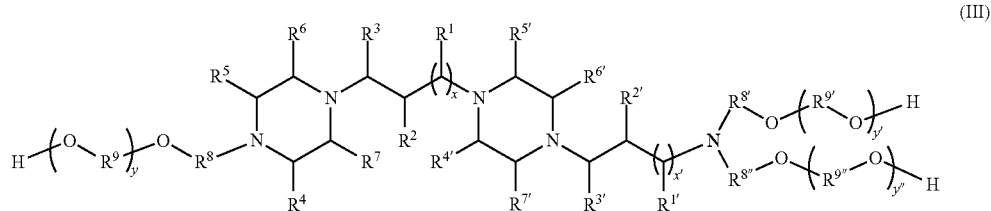

(III)

wherein $R^1$-$R^7$ and $R^{1'}$-$R^{7'}$ are independently hydrogen or hydrocarbyl groups;

x and x' are independently 0 (a covalent bond) or an integer in the range of 1-10, and if x or x' is greater than 1, then $R^1$ and $R^{1'}$ are the same or different;

y y', or y" are independently an integer ranging from 0 to 250; and $R^8$ $R^{8'}$, $R^{8''}$, $R^9$, $R^{9'}$, and $R^{9'''}$ are independently $CH_2CH_2$, $CH_2CH(CH_3)$, $CH(CH_3)CH_2$, $CH_2CH(CH_2CH_3)$, or $CH(CH_2CH_3)CH_2$, wherein if y y', or y" is greater than 1, then each corresponding $R^9$, $R^{9'}$, or $R^{9'''}$ is the same or different and in the event they are different they may be in random or block configuration.

10. A lubricant formulation comprising:
a base oil; and
a performance additive comprising the composition of claim 1.

11. A method for providing dispersancy, detergency, or both to a lubricant formulation for use in a fuel burning engine, the method comprising: including in the lubricant formulation the composition of claim 1.

* * * * *